(12) United States Patent
Hartwich

(10) Patent No.: US 11,224,664 B2
(45) Date of Patent: Jan. 18, 2022

(54) FUNCTIONALIZED METAL NANOPARTICLE

(71) Applicant: FRIZ BIOCHEM GESELLSCHAFT FÜR BIOANALYTIK MBH, Neuried (DE)

(72) Inventor: Gerhard Hartwich, Munich (DE)

(73) Assignee: FRIZ BIOCHEM GESELLSCHAFT FÜR BIOANALYTIK MBH, Munich (DE)

(*) Notice: Subject to any disclaimer, the term of this patent is extended or adjusted under 35 U.S.C. 154(b) by 407 days.

(21) Appl. No.: 16/073,296

(22) PCT Filed: Jan. 27, 2017

(86) PCT No.: PCT/EP2017/000097
§ 371 (c)(1),
(2) Date: Jul. 26, 2018

(87) PCT Pub. No.: WO2017/129365
PCT Pub. Date: Aug. 3, 2017

(65) Prior Publication Data
US 2019/0111152 A1    Apr. 18, 2019

(30) Foreign Application Priority Data

Jan. 28, 2016 (DE) .................... 10 2016 000 865.2

(51) Int. Cl.
| | |
|---|---|
| A61K 47/69 | (2017.01) |
| A61K 38/17 | (2006.01) |
| A61K 38/46 | (2006.01) |
| A61K 31/7088 | (2006.01) |
| A61K 9/14 | (2006.01) |
| B82B 1/00 | (2006.01) |
| B82B 3/00 | (2006.01) |
| B82Y 5/00 | (2011.01) |

(52) U.S. Cl.
CPC ............ *A61K 47/6923* (2017.08); *A61K 9/14* (2013.01); *A61K 38/1709* (2013.01); *A61K 38/465* (2013.01); *A61K 47/6929* (2017.08); *C12Y 301/03001* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 6,506,564 B1 | 1/2003 | Mirkin et al. | |
| 7,332,586 B2* | 2/2008 | Franzen | A61P 43/00 |
| | | | 530/402 |
| 2010/0167290 A1 | 7/2010 | Elghanian et al. | |
| 2010/0184844 A1 | 7/2010 | Mirkin et al. | |

FOREIGN PATENT DOCUMENTS

| | | | |
|---|---|---|---|
| DE | 101 55 053 B4 | 11/2005 | |
| EP | 1301625 B1 | 11/2010 | |
| WO | 2010120420 A1 | 7/2010 | |
| WO | WO-2010120420 A1 * | 10/2010 | ............ A61P 31/04 |

OTHER PUBLICATIONS

Vinogradov (2003) "DNA helix: the importance of being GC-rich", Nucleic Acids Research, 31(7): 1838-44. (Year: 2003).*
Deka, et al. (2015) "Surface Passivation Improves the Synthesis of Highly Stable and Specific DNA-Functionalized Gold Nanoparticles with Variable DNA Density", ACS Applied Materials and Interfaces, 7(2): 7033-40. (Year: 2010).*
Fischer, et al. (2011) "DNase 2 is the main DNA-degrading enzyme of the Stratum Corneum", PLoS one, 6(3): article e17581, 9 pages. (Year: 2011).*
Haque, et al. (2014) "DNA-associated click chemistry", Science China: Chemistry, 57(2): 215-231. (Year: 2014).*
Machine translation of DE101 55 053 B4.
International Preliminary Report on Patentability from International Application No. PCT/EP2017/000097 dated Feb. 19, 2018.
S.H. Wang, C.W. Lee, A. Chiou, P.-K. Wei, Journal of Nanotechnology, 2010,8,33.
H.J. Yen, S.H. Hsu, C.L. Tsai, Small 2009,5,155,3.

* cited by examiner

*Primary Examiner* — Robert M Kelly
(74) *Attorney, Agent, or Firm* — Frank Rosenberg

(57) ABSTRACT

The present invention relates to a prefunctionalized metallic nanoparticle (10) as a standardized basic building block of biofunctionalized nanoparticles (40), having a thiol-reactive metallic nanoparticle (12) that is prefunctionalized by a bifunctional molecule (20) that consists of an anchor component (22) and a short further-functionalization stub (24). Here, it is provided that the anchor component (22) comprises one or more dithiophosphate groups, and the short further-functionalization stub (24) is adapted for the attachment of a desired biofunctionalization (30) and is selected from the group consisting of
i) an unmodified standardized oligonucleotide strand (26) having 2 to 18 bases for further-functionalization with biomolecules (30) having a terminal complementary strand (36) of the standardized oligonucleotide strand (26), and
ii) a 2- to 18-base-long oligonucleotide strand (50; 60) that is modified with a terminal reactive group (52; 62) for biomolecules.

Figure 1:
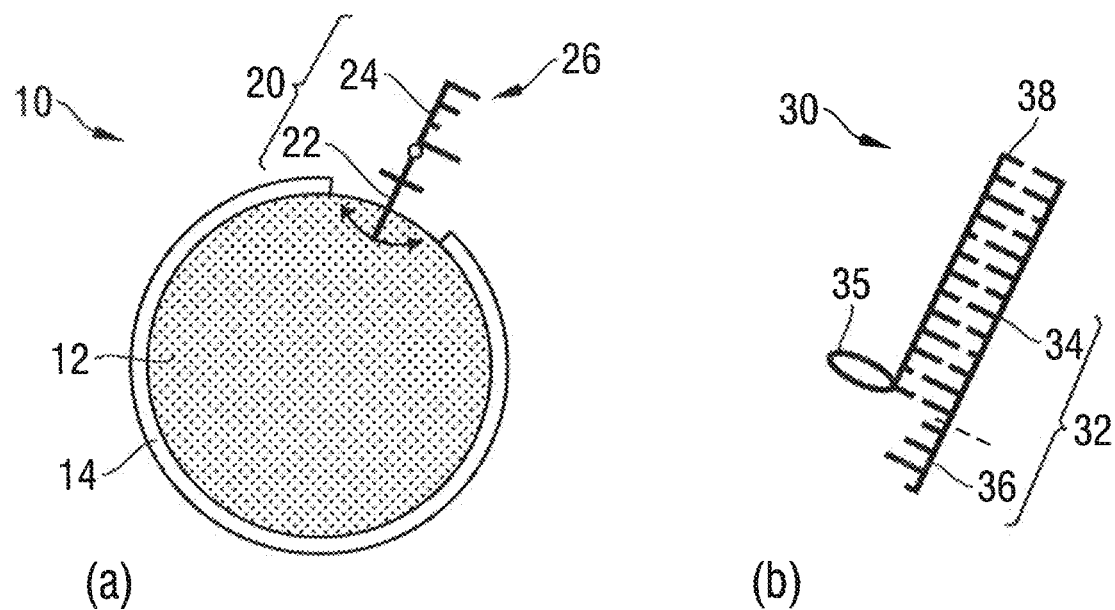
Figure 1:
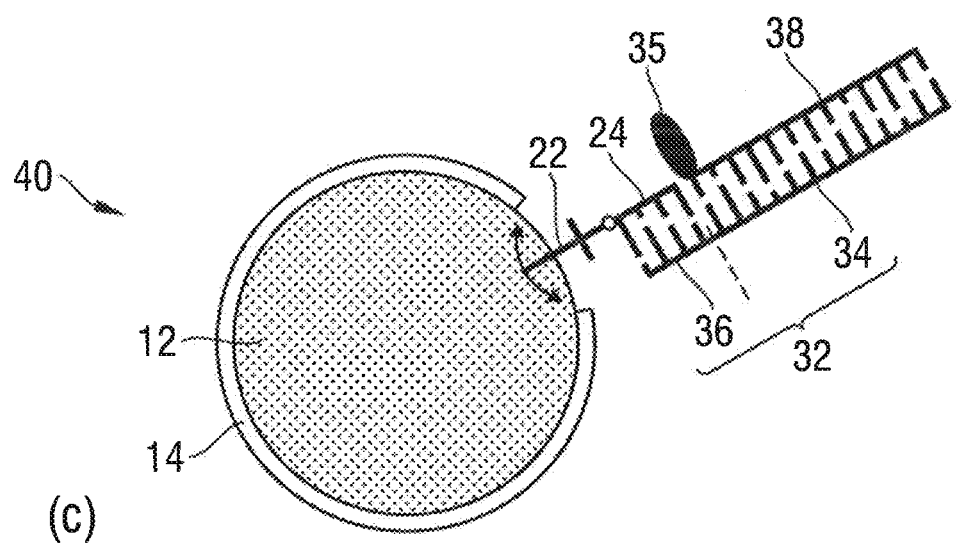

21 Claims, 7 Drawing Sheets
Specification includes a Sequence Listing.

(a)

(b)

SEQUENCE LISTING

```
<160> NUMBER OF SEQ ID NOS: 7

<210> SEQ ID NO 1
<211> LENGTH: 3
<212> TYPE: DNA
<213> ORGANISM: Artifical Sequence
<220> FEATURE:
<223> OTHER INFORMATION: synthetic sequence

<400> SEQUENCE: 1 ttt                                                          3

<210> SEQ ID NO 2
<211> LENGTH: 17
<212> TYPE: DNA
<213> ORGANISM: Artifical Sequence
<220> FEATURE:
<223> OTHER INFORMATION: synthetic sequence

<400> SEQUENCE: 2
cctcctttac cgtgatt                                           17
```

```
<210> SEQ ID NO 3
<211> LENGTH: 12
<212> TYPE: DNA
<213> ORGANISM: Artifical Sequence
<220> FEATURE:
<223> OTHER INFORMATION: synthetic sequence

<400> SEQUENCE: 3
tcaccgtaaa gg                                                              12

<210> SEQ ID NO 4
<211> LENGTH: 18
<212> TYPE: DNA
<213> ORGANISM: Artifical Sequence
<220> FEATURE:
<223> OTHER INFORMATION: synthetic sequence

<400> SEQUENCE: 4
caatcacggt aaaggagg                                                        18

<210> SEQ ID NO 5
<211> LENGTH: 17
<212> TYPE: DNA
<213> ORGANISM: Artifical Sequence
<220> FEATURE:
<223> OTHER INFORMATION: synthetic sequence

<400> SEQUENCE: 5
actgaattcc atgggtt                                                         17

<210> SEQ ID NO 6
<211> LENGTH: 18
<212> TYPE: DNA
<213> ORGANISM: Artifical Sequence
<220> FEATURE:
<223> OTHER INFORMATION: synthetic sequence

<400> SEQUENCE: 6
cctcctttac cgtgattg                                                        18

<210> SEQ ID NO 7
<211> LENGTH: 41
<212> TYPE: DNA
<213> ORGANISM: Artifical Sequence
<220> FEATURE:
<223> OTHER INFORMATION: synthetic sequence

<400> SEQUENCE: 7
caatcacggt aaaggaggga acccatggaa ttcagttctc a                              41
```

FUNCTIONALIZED METAL NANOPARTICLE

RELATED APPLICATIONS

This application is a national stage filing and claims the priority benefit of PCT/EP2017/000097 filed Jan. 27, 2017 and also claims priority to German Patent Application No. 10 2016 000 865.2, filed Jan. 28, 2016.

The present invention relates generally to functionalized metallic nanoparticles and relates particularly to prefunctionalized metallic nanoparticles as standardized basic building blocks of biofunctionalized nanoparticles. The present invention further relates to biofunctionalized metallic nanoparticles and a nanoparticle kit for manufacturing biofunctionalized nanoparticles.

The biomedical application of gold nanoparticles is steadily increasing, as well over 10,000 publications in peer-reviewed journals in the last 8 years prove. Gold nanoparticles are used, for example, as a diagnostic imaging agent in in vivo analyses or as a therapeutic agent in experimental gene and drug delivery. Especially delivery systems based on gold nanoparticles for tumor chemotherapy were analyzed extensively, since they allow for the expectation of higher efficacy of the active substance with lower cytotoxicity to healthy tissue. For the delivery of nucleic acids, compared with other "synthetic vectors" (delivery systems), such as lipid-based vectors, gold nanoparticles have the advantage that both their physical properties, for example their size and surface characteristics, and their chemical-biological properties, namely especially the multifunctional derivatizability of the surface, and thus cytotoxicity, biodistribution and in vivo excretion, are nearly arbitrarily modulatable.

On the other hand, however, this high modularity of functionalized gold nanoparticles also triggers numerous controversial discussions of the mechanisms for delivery, cell penetration, efficacy and the like in the literature, especially since the various research groups each use their own compositions of derivatized gold nanoparticles, each of these compositions differing as a result of different manufacturing methods and parameters.

Gold nanoparticles are obtained, for example, by reducing chloroauric acid H[AuCl$_4$] in boiling aqueous solution with citric acid. Colloidal nanoparticulate gold is unstable and has a tendency to coagulate/aggregate. For this reason, stabilizers such as citrates and/or detergents are commonly added. Colloidal gold nanoparticles have a strong surface plasmon absorption in the visible spectrum of light, which means they have great potential for photothermal and photometric applications.

In a study on the application of gold nanoparticles in the medical field, such as in cell experiments, it could be shown that the absorption of nanoparticles by endocytosis is dependent on size. Here, gold nanoparticles having a size of 45 nm are absorbed better by HeLa cells than 70 nm gold nanoparticles (S.-H. Wang, C.-W. Lee, A. Chiou, P.-K. Wei, Journal of Nanobiotechnology 2010, 8, 33). It is thus necessary that, in aqueous, saline solutions, the nanoparticles form a stable dispersion and form no agglomerates. Normally, however, even citrate- or detergent-stabilized gold nanoparticles are not stable in a pure cell culture medium. The result is a strong agglomeration of the nanoparticles in said medium. On the one hand, this can be prevented by the additions of proteins, such as BSA (bovine serum albumin) (H. J. Yen, S. H. Hsu, C. L. Tsai, Small 2009, 5, 1553), which coat the nanoparticles with a monomolecular protein layer of BSA and lead to an increase in the particle diameter by approximately 4-6 nm. On the other hand, this protein coating of the gold nanoparticles prevents a selective chemical derivatization of the particles in aqueous or non-aqueous systems.

From document EP 1 301 625 B1, a method and a kit for detecting an analyte in a sample is known in which metallic nanoparticle conjugates are used to which oligonucleotides are bound. From US 2010/0167290 A1, molecule-modified gold nanoparticles are known that comprise covalently bound oligonucleotides.

Proceeding from this, it is the object of the present invention to avoid the disadvantages of the background art, and especially to provide metallic nanoparticles that can be quickly, easily and nevertheless highly reproducibly provided with a desired biofunctionalization. The present invention is also intended to provide metallic nanoparticles biofunctionalized in this way.

Here, a biofunctionalization is understood, as usual, to be the adjustment of properties of a substance for safe biomedical applications.

Said object is solved by the features of the independent claims. Developments of the present invention are the subject of the dependent claims.

The present invention provides a prefunctionalized metallic nanoparticle as a standardized basic building block of biofunctionalized nanoparticles. The prefunctionalized metallic nanoparticle comprises a thiol-reactive metallic nanoparticle that is prefunctionalized by a bifunctional molecule that consists of an anchor component and a short further-functionalization stub. Here, it is provided that

- the anchor component comprises one or more dithiophosphate groups, and
- the short further-functionalization stub is adapted for the attachment of a desired biofunctionalization and is selected from the group consisting of
  i) an unmodified standardized oligonucleotide strand having 2 to 18 bases for further-functionalization with biomolecules having a terminal complementary strand of the standardized oligonucleotide strand, and
  ii) a 2- to 18-base-long oligonucleotide strand that is modified with a terminal reactive group for biomolecules.

Here, the term oligonucleotide is an equivalent to the term nucleic acid oligomer and designates a nucleic acid of a base length that is not further specified. A nucleic acid comprises at least two covalently linked nucleotides or at least two covalently linked pyrimidine (e.g. cytosine, thymine or uracil) or purine bases (e.g. adenine or guanine). The term nucleic acid refers to any "backbone" of the covalently linked pyrimidine or purine bases, such as the sugar-phosphate backbone of DNA, cDNA or RNA, a peptide backbone of PNA, or analogous structures. The term bases designates the naturally occurring nucleobases cytosine, thymine, uracil, adenine and guanine, and also their artificial analogs as long as said analogs are suitable for hybridization with complementary oligonucleotides.

Designated here as the thiol-reactive metallic nanoparticle is a metallic nanoparticle (M) that reacts with thiols (HS—R, R=residue) or disulfides (R—S—S—R), for example forming spontaneous, predominantly chemisorptive, potentially covalent or (partially) ionic interactions/bond(s) with the thiol (HS—R) or disulfide groups (R—S—S—R') of the binding partner to form adducts M-S—R or M-S—S—R, or R—S-M- . . . -M-S—R' (the ellipses indicating that it is not necessarily two directly adjacent M atoms that form the bond). In the following, the thiol-reactive metallic nanoparticle without the prefunctionalization is also often referred to as a core component of the nanoparticle.

In case ii), the terminal reactive group is advantageously an alkyne terminus for further-functionalization with azide-terminated biomolecules, an azide terminus for further-functionalization with alkyne-terminated biomolecules, is Ni-nitrilo acetic acid for further-functionalization with His-tag-terminated biomolecules, or is a biotin terminus for further-functionalization with avidin-terminated biomolecules. It is understood that, for the terminal reactive group and the corresponding complementary group of the biomolecules, also other pairs of reactive groups known to the person of skill in the art may be considered.

Here, the unmodified standardized oligonucleotide strand in case i) or the oligonucleotide strand modified with a terminal reactive group in case ii) is particularly advantageously selected in such a way that the prefunctionalized metallic nanoparticle is storage stable. Here, storage stability means that the prefunctionalized metallic nanoparticles can be stored over a period of at least 4 weeks, preferably of at least 3 months, of at least 6 months or even of at least 12 months without degrading due to contact with humidity, light and other environmental effects. The high storage stability makes it possible to break down the biofunctionalization of the nanoparticles into two sub-steps, "prefunctionalization" and "user-specific further-functionalization," to boost efficiency, since, after the laborious prefunctionalization, the nanoparticles can be stored at the manufacturer's for a lengthy period and then sold to end users. The end users can then themselves easily and user-specifically further-functionalize the nanoparticles prefunctionalized by the manufacturer, and the prefunctionalized nanoparticles and the further-functionalized nanoparticles can also be stored at the end user's over a lengthy period and be used gradually.

In the case of the user-specific further-functionalization, the prefunctionalized metallic nanoparticle is advantageously further-functionalizable through simple incubation in aqueous or non-aqueous medium.

A significant further advantage of the breakdown into the two mentioned sub-steps consists in the fact that the end user need not disclose the actual biofunctionalization to the manufacturer, but can keep it confidential and perform it himself.

For the further-functionalization stub, in case group i), in one preferred embodiment, it is provided that the oligonucleotide strand has a melting temperature above 40° C., preferably between 40° C. and 70° C. Further, the oligonucleotide strand in this case is particularly advantageously non-coding, especially non-human-genome-coding. Finally, also in case group i), it is further advantageously provided that more than 60%, preferably more than 65%, particularly preferably more than 70% of the bases of the oligonucleotide strand are guanine and/or cytosine. The oligonucleotide strand then has, for the given base length, a particularly high melting temperature.

The nanoparticle mentioned can be prefunctionalized with only one bifunctional molecule, but for most applications, it is advantageous for the nanoparticle to be prefunctionalized with multiple bifunctional molecules having the same further-functionalization stub, the coverage density advantageously even being chosen to be as high as possible. Here, an upper limit is, in practice, given by the normally desired condition that, at every further-functionalization stub, a further double-strand formation should be possible.

In one advantageous development of the present invention, the prefunctionalized nanoparticle is adapted for the attachment of multiple different biomolecules and, to this end, comprises two, three or four different bifunctional molecules, each having a different standardized further-functionalization stub. Advantageously, the different further-functionalization stubs are all formed by standardized but mutually differing oligonucleotide strands according to case group i) mentioned above. Alternatively, case groups i) and ii) can also be mixed such that, for example, one or two further-functionalization stubs according to case group ii) and one or two further-functionalization stubs according to case group i) are present.

Apart from the bifunctional molecules, the metallic surface of the nanoparticle is provided with a passivation, especially using alkane thiols or polyethylene glycols.

The anchor component preferably includes exactly one, two or three dithiophosphate groups per bifunctional molecule.

In addition to the prefunctionalized metallic nanoparticles described so far, the present invention also includes a biofunctionalized metallic nanoparticle in which a biomolecule is attached to the further-functionalization stub of a prefunctionalized metallic nanoparticle of the kind described above. It also includes a method for manufacturing a biofunctionalized metallic nanoparticle in which a biomolecule is attached to the further-functionalization stub of a prefunctionalized metallic nanoparticle of the kind described above, and finally, also relates to the use of prefunctionalized metallic nanoparticles of the kind described above for attaching biomolecules.

Here, in the mentioned nanoparticle, the method or the use, it can be provided that the biomolecule is formed by a nucleic acid oligomer, especially a single- or partially double-stranded nucleic acid oligomer or a protein.

The present invention further includes a nanoparticle kit for manufacturing biofunctionalized nanoparticles that includes prefunctionalized metallic nanoparticles as standardized basic building blocks, and in which each basic building block is formed by a thiol-reactive metallic nanoparticle that is prefunctionalized by one or more bifunctional molecules, each of which consists of an anchor component and a short further-functionalization stub. Here, it is provided that the anchor component for each bifunctional molecule of a basic building block comprises one or more dithiophosphate groups, the short further-functionalization stub for each bifunctional molecule of a basic building block is adapted for the attachment of a desired biofunctionalization and consists of an unmodified oligonucleotide strand having 2 to 18 bases for further-functionalization with biomolecules having a terminal complementary strand of the oligonucleotide strand, and the unmodified oligonucleotide strand of each of the bifunctional molecules of a basic building block being selected from a basic set of predetermined unmodified oligonucleotide strands that includes four or fewer unmodified oligonucleotide strands.

Here, in one advantageous embodiment, it is provided that the nanoparticle kit includes first standardized basic building blocks whose bifunctional molecules include only one different further-functionalization stub, which is formed by a first unmodified oligonucleotide strand from the mentioned basic set, and includes second standardized basic building blocks whose bifunctional molecules include exactly two different further-functionalization stubs, which are formed by the mentioned first unmodified oligonucleotide strand and a second unmodified oligonucleotide strand from the mentioned basic set.

The nanoparticle kit preferably further includes third standardized basic building blocks whose bifunctional molecules include exactly three different further-functionalization stubs, which are formed by the mentioned first and second unmodified oligonucleotide strand and a third unmodified oligonucleotide strand from the mentioned basic set.

In one expedient embodiment, the nanoparticle kit further includes fourth standardized basic building blocks whose bifunctional molecules include exactly four different further-functionalization stubs, which are formed by the mentioned first, second and third unmodified oligonucleotide strand and the fourth unmodified oligonucleotide strand in the mentioned basic set.

In all embodiments, the nanoparticle kit can include basic building blocks having a different particle size and/or a different thermal and/or chemical stability of the anchored further-functionalization stubs and/or a different coverage density with the bifunctional molecules and/or a different coadsorbate for passivation of the free metallic nanoparticle surface. For example, the above-mentioned first standardized basic building blocks can be present in different particle sizes, or the further-functionalization stubs of the first standardized basic building blocks can be attached to the metal surface via a different number of dithiophosphate groups (especially 1, 2 or 3).

Here, the prefunctionalized metallic nanoparticles that form the basic building blocks are advantageously storage stable, as already described in greater detail above.

The prefunctionalized metallic nanoparticles and the biofunctionalized metallic nanoparticles preferably each comprise, as a core component, one gold nanoparticle, with, however, other thiol-reactive metals, such as silver, platinum or iron, also being able to be considered as the material of the core component of the nanoparticles.

Within the scope of this description, particles having a dimension below 250 nm are designated as nanoparticles, the size specification referring to the core component, that is, the nanoparticles without the attached pre- or further-functionalizations. The size of the nanoparticles is advantageously even below 100 nm, especially between 5 nm and 50 nm. Currently, substantially spherical nanoparticles are preferred; however, in addition to spherical nanoparticles, also differently shaped particles can be used as the core component, for example ellipsoid, cuboid, rod-shaped or polyhedral particles. For anisotropic particle shapes, the size specification refers to the largest dimension of the particle.

Advantages of the present invention and further exemplary embodiments are explained below by reference to the drawings, in which a depiction to scale and proportion was dispensed with in order to improve their clarity.

Figure 2:
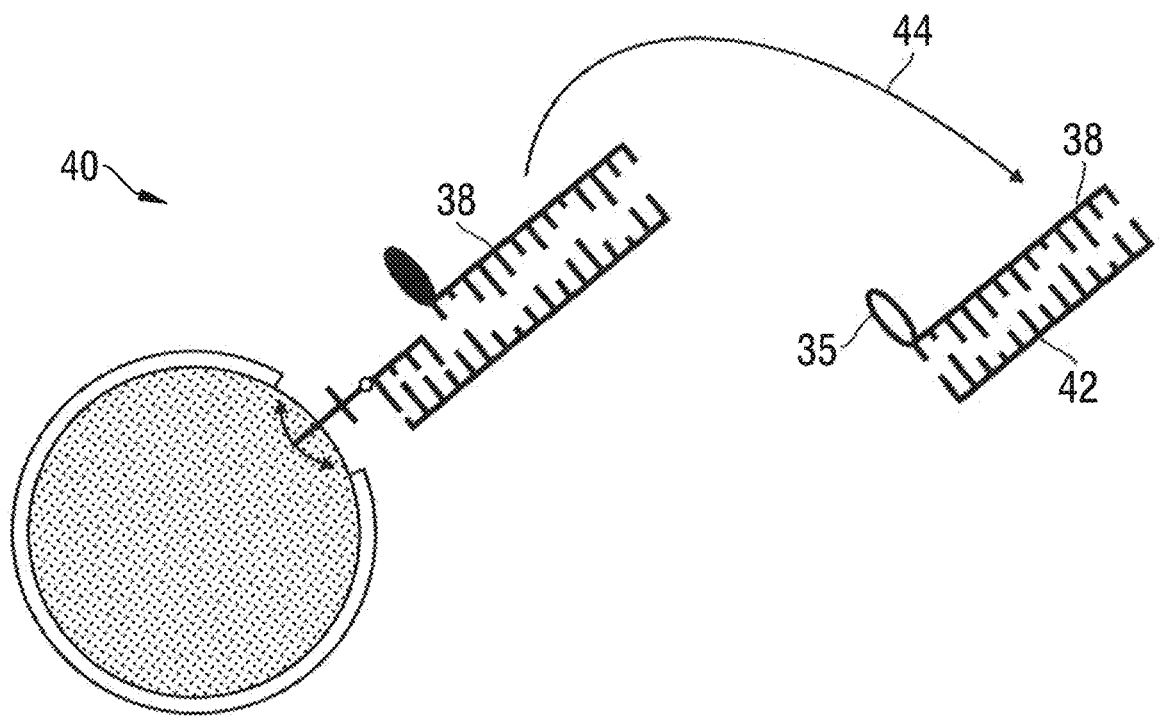
Figure 3:
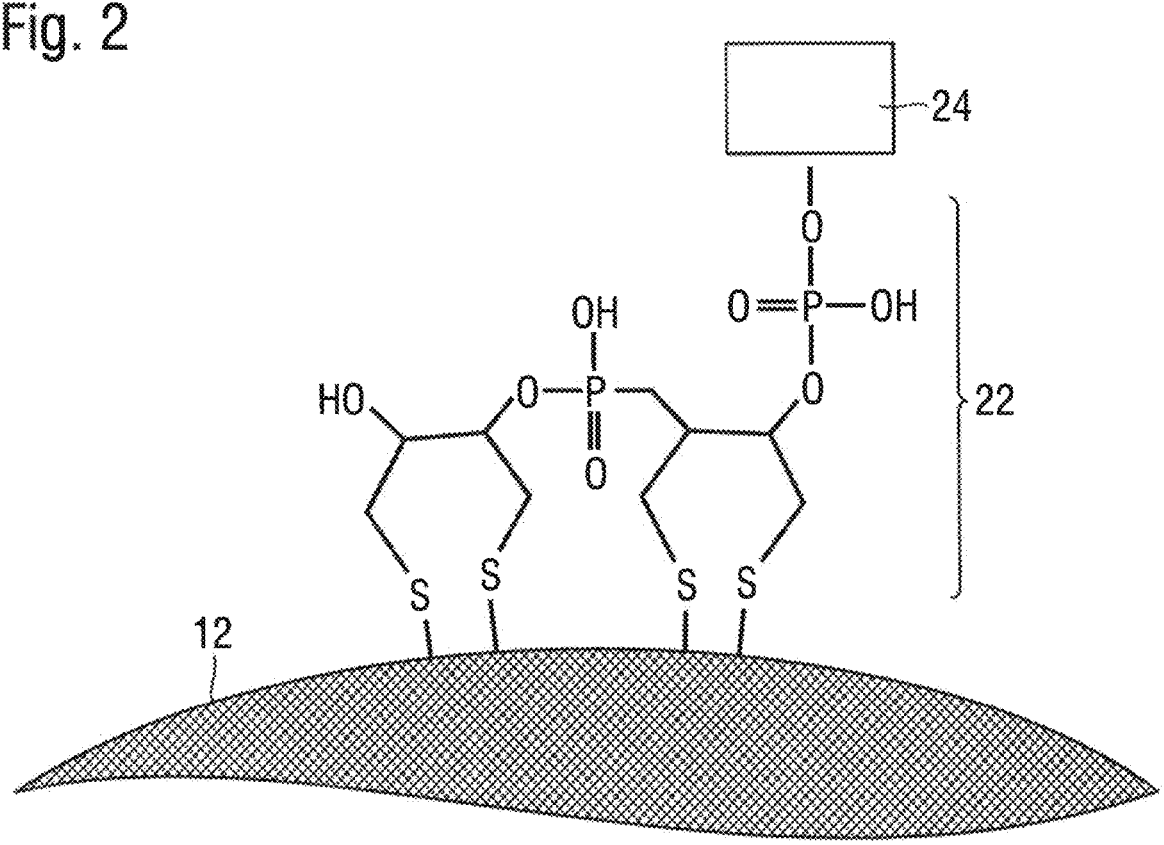
Figure 4:
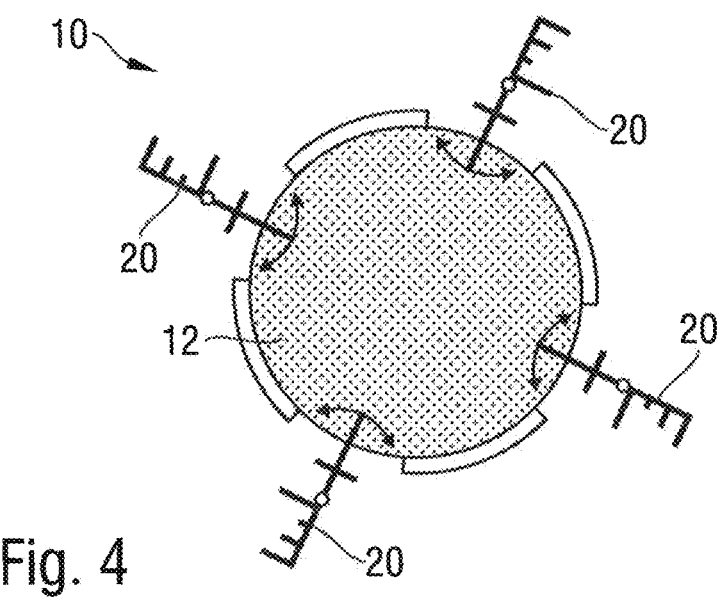
Figure 5:
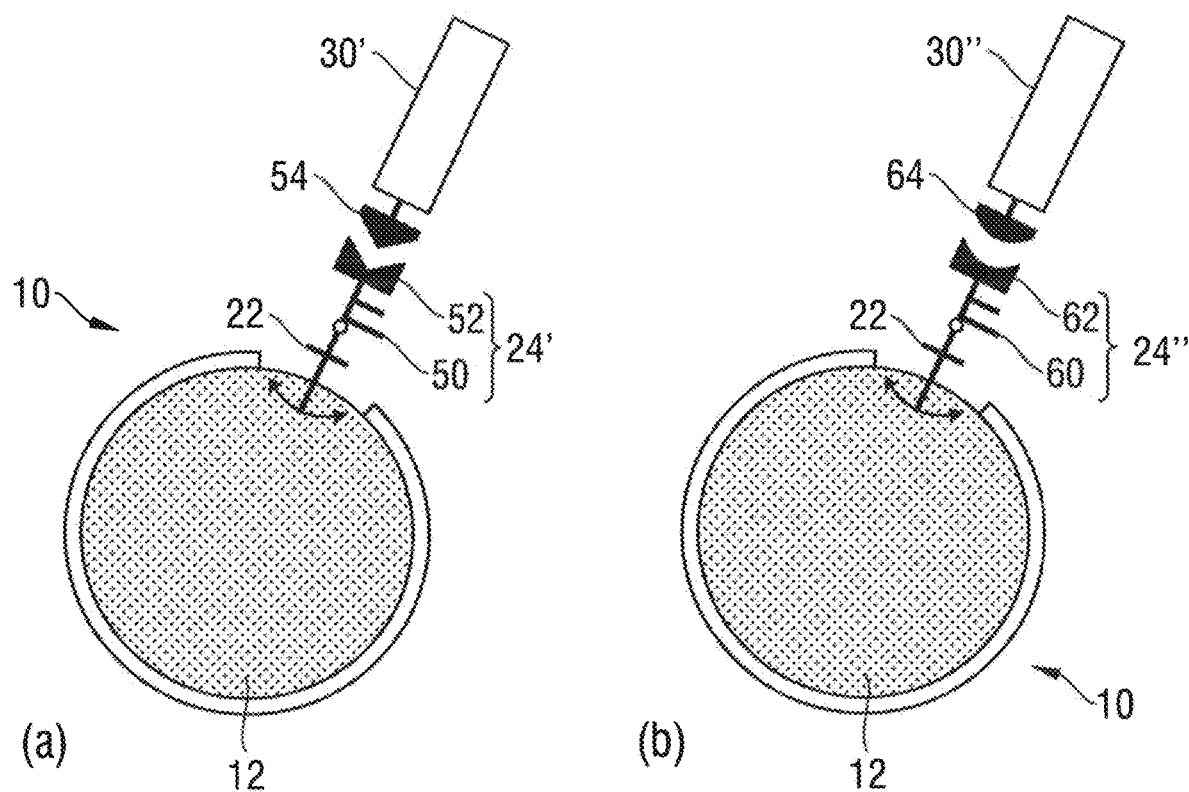
Figure 6:
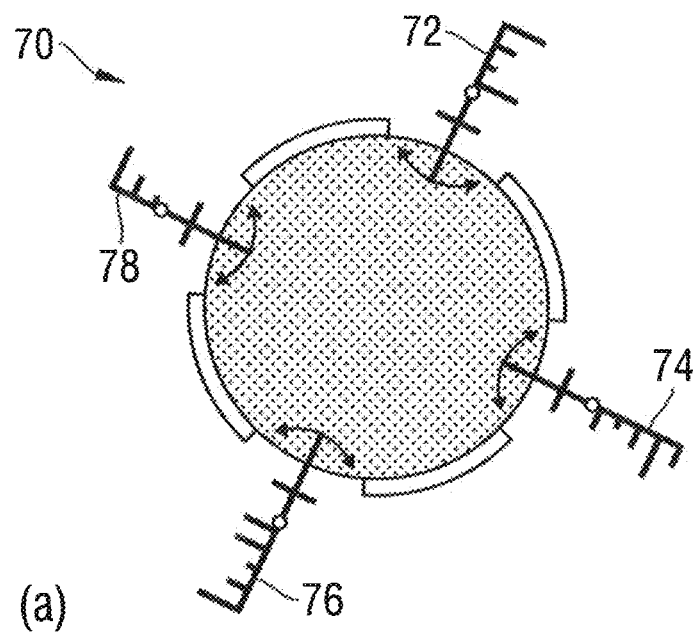
Figure 6:
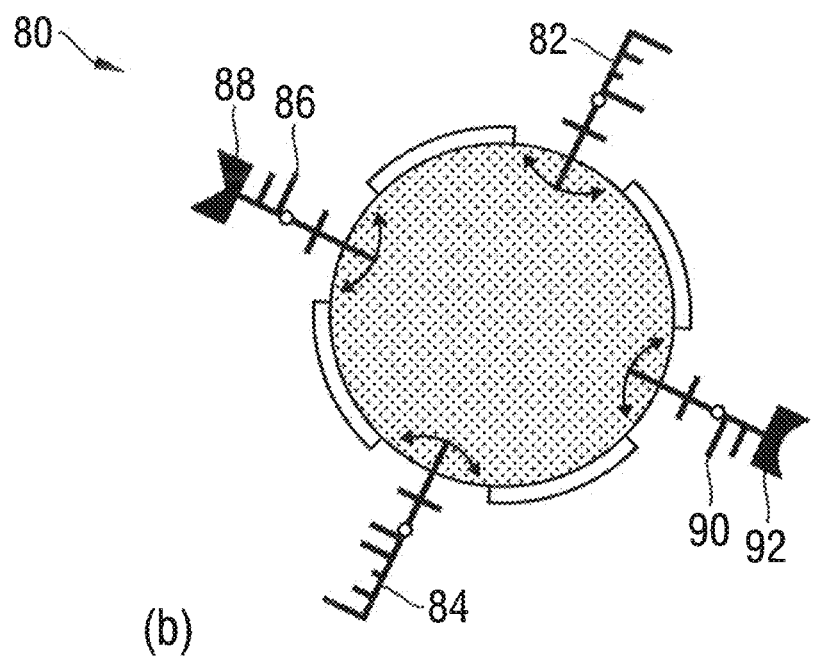
Figure 7:
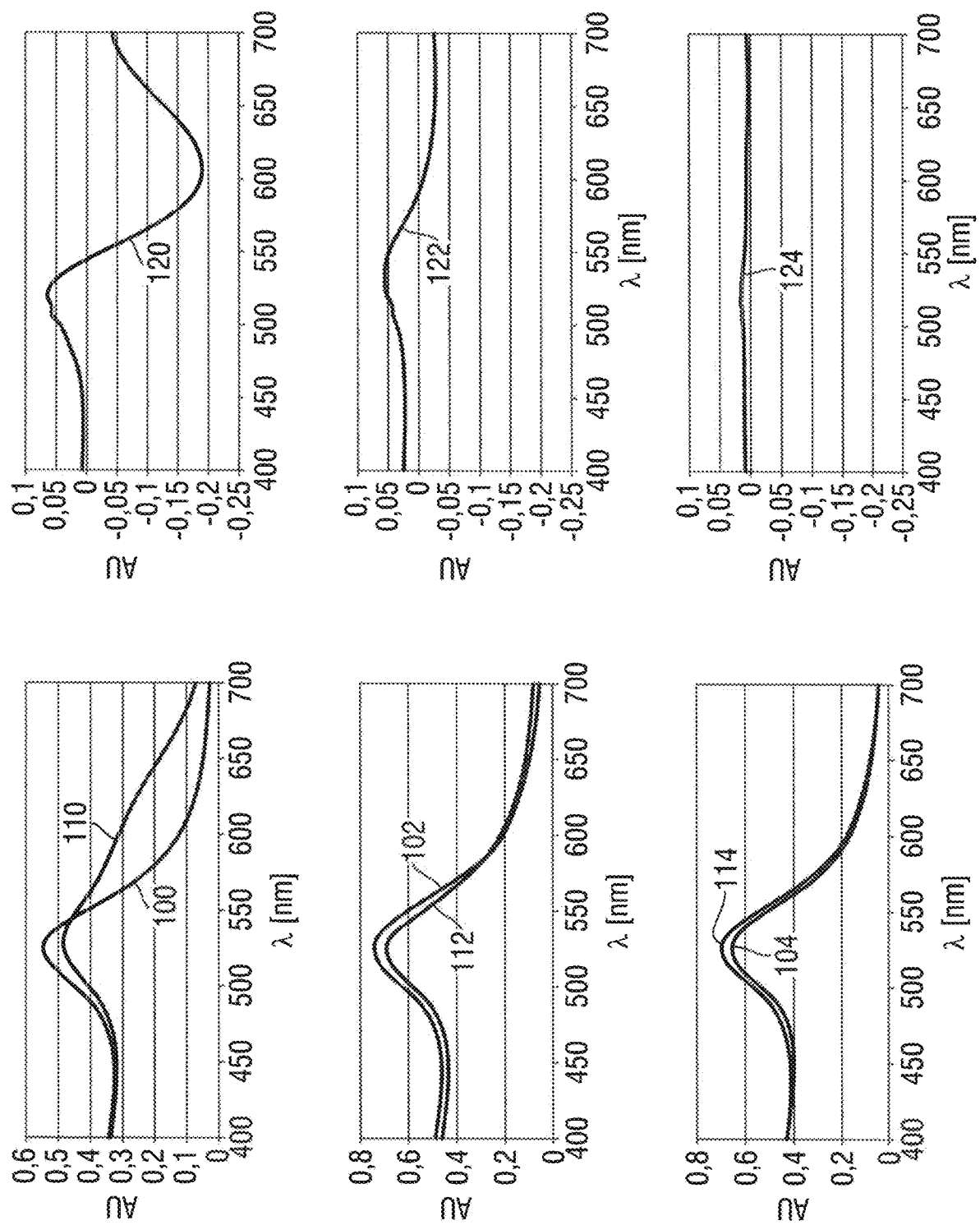
Figure 8:
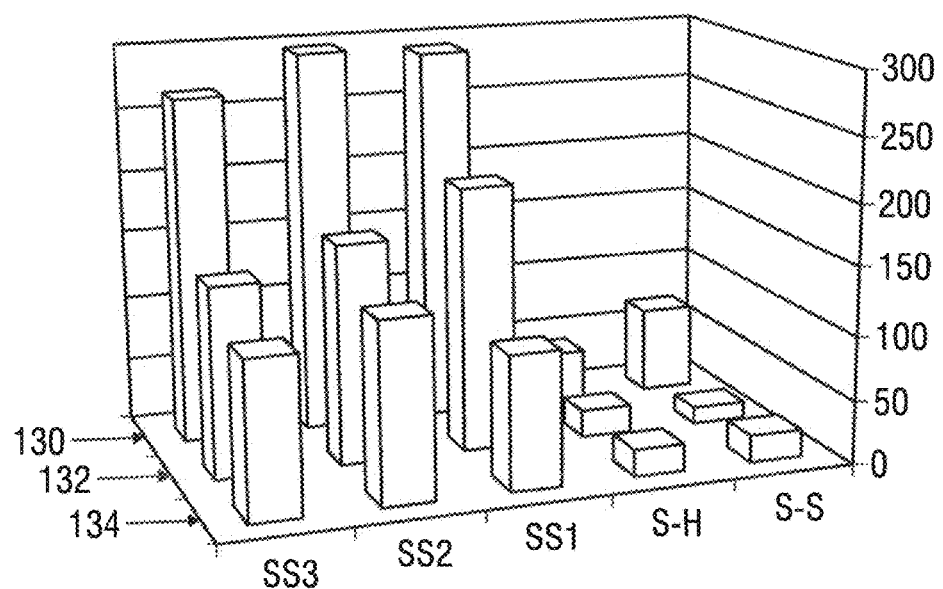
Figure 9:
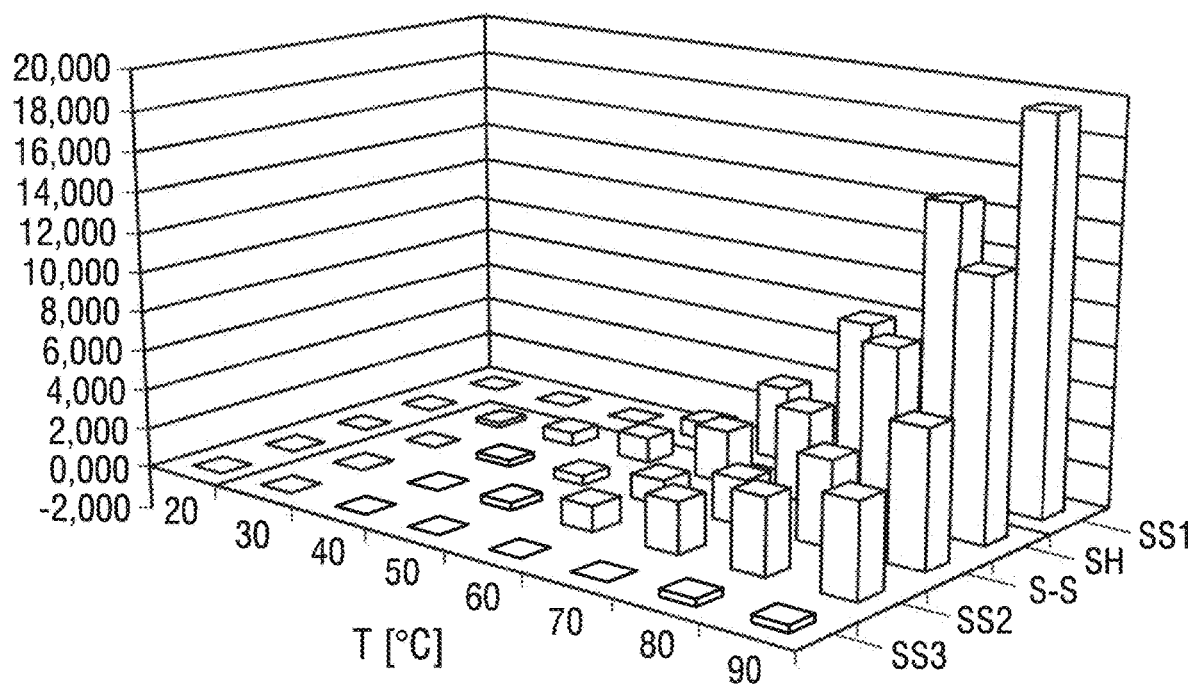
Figure 10:
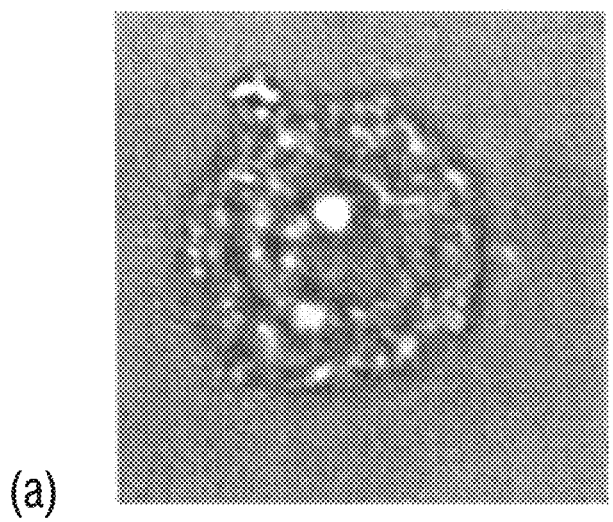
Figure 10:
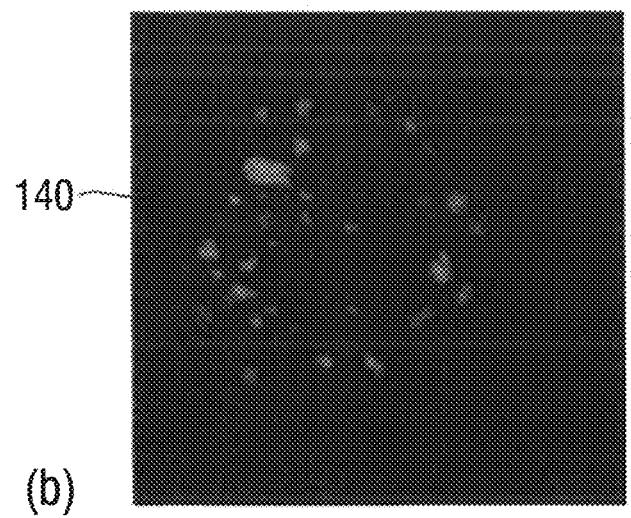

Shown are:

FIG. 1 in (a), schematically, a prefunctionalized gold nanoparticle that serves as a basic building block of biofunctionalized nanoparticles, in (b), a biomolecule adapted for attachment to the further-functionalization stub of the gold nanoparticle in FIG. 1, and in (c), the biofunctionalized gold nanoparticle created by attaching the biomolecule in (b), FIG. 2 the elution of the fluorophore-labeled complementary strand from the biomolecule of the biofunctionalized nanoparticle in FIG. 1(c) by a target RNA, FIG. 3 schematically, a section of the surface of the gold nanoparticle in FIG. 1 in the region of the attached bifunctional molecule, FIG. 4 a prefunctionalized gold nanoparticle having multiple similar bifunctional molecules, FIG. 5 in each of (a) and (b), a prefunctionalized gold nanoparticle having alternative further-functionalization stubs and, in each case, an appropriately developed biomolecule to be attached, FIG. 6 in (a) and (b), two exemplary embodiments for gold nanoparticles to which four different bifunctional molecules, each having different further-functionalization stubs, are attached, FIG. 7 left, in each case, absorption spectra of various gold nanoparticle types in aqueous solution immediately after addition of 6×PBS and the same solution after 120 min.; right, each of the differential spectra are shown, FIG. 8 measurement results for (maximum) coverage depending on the anchor function/accessibility, FIG. 9 measurement results for the quantity-standardized gold-nanoparticle-thiol temperature stability, and FIG. 10 in (a), a transmitted-light image, and in (b), a fluorescence microscopy image of a macrophage that was stimulated to express miRNA 146a and incubated with functionalized gold nanoparticles.

The present invention will now be explained using the example of functionalized gold nanoparticles, but it is not limited to the gold nanoparticles shown for illustration, but rather can also be used with other nanoparticles having thiol-reactive metallic surfaces, such as silver or platinum nanoparticles.

For this, FIG. 1(a) shows a prefunctionalized gold nanoparticle 10 whose functionalization 20, while it itself constitutes no biofunctionalization, permits an end user to quickly and easily provide the preprepared nanoparticle, for example through incubation in aqueous or non-aqueous medium, with an arbitrary desired biofunctionalization 30 (FIG. 1(b)). The functionalization 20 of the nanoparticle 10 is thus referred to within the scope of this description as a prefunctionalization, since it precedes and prepares the desired biofunctionalization.

The core component of the prefunctionalized gold nanoparticles 10 is formed by a substantially spherical gold nanoparticle 12 having a diameter of about nm. The spherical gold nanoparticle 12 is prefunctionalized by a bifunctional molecule 20 that consists, in its first function, of an anchor component 22 for anchoring to the gold surface of the core component, and in its second function, of a short further-functionalization stub 24 that is adapted for the attachment of the desired biofunctionalization.

Here, the anchor component 22, depicted only schematically in FIG. 1, comprises one or more dithiophosphate groups that ensure a stable anchoring of the molecule 20 to the gold surface of the nanoparticle 12, as explained in greater detail below in connection with FIG. 3.

In the exemplary embodiment in FIG. 1, the short further-functionalization stub 24 linked with the anchor component 22 is formed by a standardized oligonucleotide strand 26 having four bases. The further-functionalization stub 24 itself is non-coding, especially non-human-genome-coding, and serves exclusively as a specific docking station for suitably prepared biomolecules.

In the regions not covered with bifunctional molecules 20, the free gold surface of the nanoparticle 12 is provided with a passivation 14, in the exemplary embodiment for instance using polyethylene glycols.

For the attachment to the nanoparticle 12, as shown in FIG. 1(b), the desired biomolecules 30 must comprise a terminal complementary strand 36 to the oligonucleotide strand 26 of the further-functionalization stub 24. The oligonucleotide strand 26 of the gold nanoparticle 10 and the terminal complementary strand 36 of the biomolecule 30 fit each other like a key and lock, so that it is ensured that only biomolecules 30 that have been prepared with a suitable complementary strand 36 can attach to the prefunctionalized gold nanoparticle 10.

In the concrete exemplary embodiment, the biomolecule 30 consists, for instance, of a longer oligonucleotide 32 having a desired useful region 34 to which the already mentioned terminal complementary strand 36 attaches. In the useful region 34, the oligonucleotide 32 is hybridized with a complementary strand 38 that is labeled with a fluorophore 35 and that targets a certain cell-specific mRNA for gene expression analysis.

An important distinctive feature of the present invention now consists in the biomolecule 30 in FIG. 1(b) being able, thanks to the prefunctionalization, to be attached to the prefunctionalized gold nanoparticle 10 in FIG. 1(a) ideally in just a few minutes through simple pipetting steps, thus creating the particle 40, provided with the desired biofunctionalization, shown in FIG. 1(c).

In the biofunctionalized nanoparticle 40 shown in the exemplary embodiment, the fluorescence of the attached fluorophore 35 is first quenched by the immediate proximity of the gold surface 12. If the nanoparticle 40 encounters the target RNA 42 in a cell, the fluorophore-labeled complementary strand 38 is eluted from the biomolecule 30 (arrow 44) by hybridization with the mRNA and the fluorophore 35 can be fluorometrically detected, as depicted schematically in FIG. 2.

In principle, a gold nanoparticle 12 can, of course, also be directly functionalized with a desired biomolecule 30 (without the terminal complementary strand 36) without prefunctionalization 20, as is already described in the background art. However, such a biofunctionalization of gold nanoparticles normally succeeds only in an often multi-day procedure by well-trained staff and, accordingly, entails high costs. This can constitute an obstacle especially when a large number of different biomolecules 30 are to be attached to gold nanoparticles or when the results of biofunctionalizations of different research groups are to be compared with each other. Since each group usually uses its own compositions of derivatized gold nanoparticles, even nanoparticles functionalized with nominally identical biomolecules often have different properties, such that, in some cases, results of different research groups can hardly be correlated.

The prefunctionalized gold nanoparticles 10 now proposed provide effective relief here. Through the use of standardized oligonucleotide strands 26 in the further-functionalization stub 24, a nanoparticle kit with highly reproducible basic material having customized properties can be provided for any desired applications or analyses. The complex biofunctionalization of nanoparticles is broken down by the present invention into two sub-steps, namely a standardized prefunctionalization, on the one hand, and a user-specific further-functionalization on the other.

Here, as the first functionalization of the gold nanoparticles, the prefunctionalization is the sub-step with high complexity in terms of time, equipment and personnel, and requires great know-how and extensive experience in the functionalization of gold surfaces. According to the present invention, said prefunctionalization is now carried out in a standardized way only for a relatively small number of different prefunctionalizations in a nanoparticle kit and is done centrally by a provider of prefunctionalized nanoparticles. The end user obtains the prefunctionalized nanoparticles from the provider and need not have the required knowledge and equipment resources for the first functionalization himself. The storage stability of the prefunctionalized gold nanoparticles ensures that the two steps "prefunctionalization" and "further-functionalization" can be temporally and spatially decoupled from one another.

Proceeding from the prefunctionalized nanoparticles, the further-functionalization can then be carried out very easily and quickly by the end user and can also be done by personnel with little training with a few pipetting steps. In addition to the low effort, time and cost involved, this especially also has the advantage that the end user can quickly manufacture a plurality of different biofunctionalized nanoparticles with the same basic material, such that a high comparability of the results is ensured. Since the further-functionalization can be carried out by the end user himself, said end user additionally need not give third parties potentially sensitive information about the biomolecules to be attached, which can be of great importance particularly in research and development projects.

To explain the operating principle of the anchor component 22 in greater detail, FIG. 3 shows, schematically, a section of the surface of the gold nanoparticle 12 in the region of the attached bifunctional molecule 20.

For the anchoring, the further-functionalization stub 24, here in the form of a standardized oligonucleotide strand 26, was provided at its 3' end, by means of 1,2-dithian-4-O-dimethoxytrityl-5-[(2-cyanoethyl)-N,N-diisopropyl)]-phosphoramidite (DTPA), with dithiol modifications, which can form a stable thiol anchor on the gold surface the nanoparticle 12. Here, FIG. 3 shows a specific exemplary embodiment having two dithiophosphate groups. If a lower thermal and/or chemical stability of the anchoring is desired, the attachment can be done, instead, with an anchor component having only one dithiophosphate group, and in the event of a desired higher thermal and/or chemical stability, the attachment can be done with an anchor component having three dithiophosphate groups.

In this way, thermal and/or chemical stability of the anchoring of the further-functionalization stub 24 can be chosen to be different as desired. A nanoparticle kit can therefore, for example, also include nanoparticles having the same further-functionalization stub, but a differently stable anchoring of the further-functionalization stub.

A prefunctionalized gold nanoparticle 10 can, of course, include not only a bifunctional molecule, as shown in FIG. 1 for the sake of simpler illustration. Rather, for a desired further-functionalization function, multiple similar bifunctional molecules 20 are advantageously attached to a gold nanoparticle 12, as illustrated in FIG. 4. Here, the coverage density is advantageously even chosen to be as high as possible, which means, in practice, that the coverage density is chosen to be so high that, at each further-functionalization stub, a double-strand formation is just barely possible.

In addition to the further-functionalization functions in the form of an oligonucleotide strand described so far, with reference to FIG. 5(a), also embodiments may be considered in which the further-functionalization stub 24' of a prefunctionalized gold nanoparticle 12 consists of an ultrashort oligonucleotide 50 having an alkyne terminus 52. The biomolecules 30' to be attached must, in this case, be provided with an azide terminus 54, as likewise depicted schematically in FIG. 5(a). The ultrashort oligonucleotide 50 that serves to attach the alkyne terminus 52 to the anchor component 22 comprises 2 to 18, preferably even only 2 to 8 bases.

Copper-catalyzed alkyne-azide cycloaddition (CuAAC) is an example of a so-called click reaction. It is highly selective and proceeds practically only between the components azide and alkyne. The reaction is also not affected by most other organic groups that occur in biomolecules to be attached, such as amino and carboxyl groups. Moreover, azides and alkynes do not occur in native biomolecules. Alkyne modifications can be produced, for example, in a standard oligosynthesis with alkyne phosphoramidite. Proteins labeled with azide and alkyne groups can be manufactured, for instance, using amino-reactive azido-NHS ester or alkyne-NHS ester, or biotechnologically with the appropriate modified amino acid building blocks.

A further possibility consists in forming the further-functionalization stub 24" of a prefunctionalized gold nanoparticle 12 from an ultrashort oligonucleotide 60 and a terminal Ni-nitrilo acetic acid 62. In this case, the biomolecules 30" to be attached must have a His-tag terminus 64, as shown schematically in FIG. 5(b). Also in this variant, the ultrashort oligonucleotide 60 that serves to attach the Ni-nitrilo acetic acid terminus 62 to the anchor component 22 comprises only 2 to 18, preferably even only 2 to 8 bases.

The embodiments in FIG. 5 likewise use the key-lock principle for attaching the biomolecules, since the alkyne terminus 52 of the further-functionalization stub 24' of the gold nanoparticle 10 and the azide terminus 54 of the biomolecules 30' (FIG. 5a), or the terminal Ni-nitrilo acetic acid 62 of the further-functionalization stub 24" of the gold nanoparticle 10 and the His-tag terminus 64 of the biomolecule 30" (FIG. 5b) fit each other, in each case, like a key and lock. In this way, it is ensured that only appropriately modified biomolecules 30' and 30", in each case, can attach with their respective "key" 54 and 64 to the "lock" 52 and 62 affixed to the prefunctionalized gold nanoparticle.

The prefunctionalized gold nanoparticles can also comprise multiple different further-functionalization stubs in order to be specifically further-functionalizable. For this, as illustrated in FIG. 6, to a gold nanoparticle can be attached bifunctional molecules that especially comprise two, three or four different further-functionalization stubs. In the exemplary embodiment in FIG. 6(a), the prefunctionalized gold nanoparticle 70 includes four different bifunctional molecules, each having a different further-functionalization stub. The further-functionalization stubs in FIG. 6 are, by way of example, all formed by standardized but mutually differing oligonucleotide strands 72, 74, 76, 78, each having 3 to 5 bases.

The exemplary embodiment in FIG. 6(b) shows a prefunctionalized gold nanoparticle 80 in which two of the bifunctional molecules comprise further-functionalization stubs in the form of different standardized oligonucleotide strands 82, 84, while a third further-functionalization stub consists of an ultrashort oligonucleotide 86 having an alkyne terminus 88 and a fourth further-functionalization stub consists of an ultrashort oligonucleotide 90 having a terminal Ni-nitrilo acetic acid 92.

While, so far, only individual, prefunctionalized gold nanoparticles were shown to explain the inventive principle, the present invention especially also includes a nanoparticle kit for manufacturing biofunctionalized nanoparticles. Such a kit includes a number of standardized basic building blocks in the form of prefunctionalized gold nanoparticles of the kind described above. Here, to achieve the mentioned standardization, a basic set of oligonucleotide strands is specified that includes only one, two, three or four elements. For example, a basic set M is specified that includes four different oligonucleotide strands A, B, C, D, each having 2 to 18 bases.

As already generally explained above, the oligonucleotide strands A, B, C, D are advantageously non-coding, especially non-human-genome coding, and have a melting temperature above 40° C., especially between 40° C. and 70° C. Here, especially more than 60%, 65% or even 70% of the bases of the oligonucleotide strands can be guanine and/or cytosine.

Each prefunctionalized gold nanoparticle that may be considered as a standardized basic building block of the kit is prefunctionalized by one or more bifunctional molecules of the kind described above, the short further-functionalization stubs of the bifunctional molecules being selected exclusively from the basic set M, that is, having to be formed by one or more of the oligonucleotide strands A, B, C or D.

Specifically, a nanoparticle kit according to the present invention includes, as a first standardized basic building block $B_1$, prefunctionalized gold nanoparticles whose bifunctional molecules include only one different further-functionalization stub, which is formed by an oligonucleotide strand from the mentioned basic set M. There are thus four first basic building blocks, namely $B_1=\{AuNP:A, AuNP:B, AuNP:C, AuNP:D\}$, the designation AuNP:X meaning that the further-functionalization stub(s) of the gold nanoparticle (=AuNP) is/are formed by the oligonucleotide strand X. It is understood that a prefunctionalized gold nanoparticle AuNP:X can include multiple similar bifunctional molecules having the same oligonucleotide strand X to increase the coverage density. The simplest nanoparticle kit $K_1$ now consists of only the four basic building blocks $B_1$, that is, $K_1=B_1$.

The next more complex kit is obtained when there are added to the first basic building blocks $B_1$ second standardized basic building blocks in which the bifunctional molecules include exactly two different further-functionalization stubs that are formed by a first or second oligonucleotide strand from the mentioned basic set M. There are thus six second basic building blocks, namely $B_2=\{AuNP:A,B, AuNP:A,C, AuNP:A,D AuNP:B,C,$
    $AuNP:B,D, AuNP:C,D\}$, the designation AuNP:X,Y meaning, accordingly, that some of the further-functionalization stubs of the gold nanoparticle are formed by the oligonucleotide strand X and some by the oligonucleotide strand Y. The more complex nanoparticle kit $K_2$ thus consists of the ten first and second basic building blocks $K_2=B_1\cup B_2$.

A third kit further includes, in addition to the basic building blocks $B_1$ and $B_2$, third standardized basic building blocks $B_3$ whose bifunctional molecules include exactly three different further-functionalization stubs, which are formed by three different oligonucleotide strands from the mentioned basic set M. There are four such third basic building blocks, namely $B_3=\{AuNP:A,B,C, AuNP:A,B,D, AuNP:A,C,D, AuNP:$
    $B,C,D\}$, such that the third kit $K_3=B_1\cup B_2\cup B_3$ includes 14 basic building blocks. Finally, the complete kit $K_4$ based on the basic set M also includes, in addition to the mentioned basic building blocks $B_1$, $B_2$ and $B_3$, the standardized basic building block that includes all four oligonucleotide strands of the basic set M as further-functionalization stubs, $B_4=\{AuNP:A,B,C,D\}$, and $K_4=B_1 \cup B_2 \cup B_3 \cup B_4$. With such a kit $K_4$, up to four different biomolecules can be attached, in any desired combination and sequence, to appropriate fitting basic building blocks of the kit. The basic building blocks are standardized, since they include only oligonucleotide strands from the specified set M.

In one modification, a nanoparticle kit $K_5$ based on the mentioned basic set M includes, for each number of different further-functionalization stubs, only one basic building block each, so for example $$K_5=\{AuNP:A, AuNP:A,B, AuNP:A,B,C, AuNP:A,B,C,D\}$$

When said kit $K_5$ is used, the first biomolecules to be attached must always be terminated with the complementary strand to the oligonucleotide strand A, the second biomolecules to be attached, with the complementary strand to the oligonucleotide strand B, the third biomolecules to be attached, with the complementary strand to the oligonucleotide strand C, and the fourth biomolecules to be attached, with the complementary strand to the oligonucleotide strand D.

In addition to the mentioned different prefunctionalizations, a nanoparticle kit can also include nanoparticles of different particle size, different thermal and/or chemical stability of the prefunctionalizations, different coverage density with the prefunctionalization functions, and/or different coadsorbate for passivation.

The manufacture of prefunctionalized gold nanoparticles (AuNP) according to the present invention, advantageous properties of the same, and some exemplary embodiments and applications are described in greater detail below.

EXAMPLE 1: PREPARING AUNP BUILDING BLOCKS HAVING OLIGONUCLEOTIDE ANCHOR FUNCTIONS

Multiple methods for derivatizing gold nanoparticles are known, for instance the so-called salting-out method, in which the attachment of thiol-modified oligonucleotides to citrate-stabilized gold NP in aqueous solution is accomplished by increasing the salt concentration of the solution over several days.

However, a slow increase in the salt concentration may be achieved not only, as is currently common, by adding small amounts of salt over a long period, but also by continuously evaporating the solution (concentrating). This can be achieved simply and reproducibly in a vacuum concentrator (Speed Vac). Here, the time required is reduced to about 2 hours. The isolation of the derivatized AuNP from the starting solution is done by (repeatedly) ultracentrifuging and resuspending the pelleted AuNP. Other purification methods using chromatography, size exclusion, etc. are far more complex than a single or repeated centrifugation and are less complete.

It was found that, in this way, also routinely mixed derivatizations succeed, that is, the simultaneous attachment of different thiol-modified oligonucleotides, if said oligonucleotides are offered in the appropriate molar ratio, where the mole fraction x of the under-represented oligonucleotide is to be used in the ratio $1.4 \, x/\sqrt{1-x}$ to achieve an x to $(1-x)$ attachment of two different oligonucleotides.

The passivation of the AuNP must, regardless of the type of passivation, occur after attachment of the anchor oligos, but ideally before the purification by centrifugation, through incubation with the passivation substances (normally alkane thiols or polyethylene glycols, PEG) in the concentration 10 mM over approximately 15 min. A passivation simultaneously with the attachment of the anchor oligos does not result in a uniform attachment and passivation behavior.

The coverage density of the AuNP with thiol-oligonucleotide anchors can be determined through the choice of the oligonucleotide concentration ratios "oligonucleotides to unmodified nanoparticles," but also through the number of thiol functions. This method is also well suited for the attachment of double strands and complex constructs. Here, the coverage density of the nanoparticles can be specifically varied via the number of thiol functions and thus via the "footprint" of the anchor function. Specific variations of the coverage of 20 nm nanoparticles with 1-3, 10 (+2), 20 (+2), 40 (+3) and 60 (+3) attachment oligos succeed. For an optimum further-functionalization with the oligonucleotide-modified AuNP with further oligonucleotides through complementary-strand hybridization, in addition to the specific coverage density, it is important to attach the oligonucleotide derivatizations to the citrate-stabilized AuNP in the form of double strands and to subsequently remove the (non-thiol-modified) complementary strand from the AuNP. This is achieved simultaneously with the purification through centrifugation/isolation of the prefunctionalized AuNP in that the AuNP are centrifuged at a temperature that is just above the melting point of the slightly modified double-stranded oligonucleotides.

In the isolate obtained through centrifugation and comprising oligonucleotide-derivatized AuNP, also AuNP educts can be included; their proportion can be—in the event of a desired high coverage density—substantially reduced if the thiol-modified oligonucleotides in the starting solution are used in substantial molar excess (e.g. 10- to 50-fold molar excess).

EXAMPLE 2: AGGLOMERATION

Unmodified AuNP are unstable in saline solutions and tend to agglomerate. This results in, among other things, unmodified AuNP being difficult to resuspend following pelleting by (ultra-) centrifugation (which in turn can be exploited to separate the unmodified AuNPs from (more easily resuspendable, vide infra) modified AuNPs). The extent of such an agglomeration can easily be traced using the absorption properties of suspended/dissolved AuNP.

The absorption is described by the Beer-Lambert law ($A=\log(I_0/I)=\varepsilon c l$; A: absorption, $I_0$: intensity of the incoming light beam, I: intensity of the outgoing light beam, $\varepsilon$: absorption/extinction coefficient, c: concentration and l: layer thickness). Since the optical properties in the UV-Vis spectrum are determined by the surface plasmons of the gold, which are size-dependent, the agglomeration can be tracked photospectrometrically: accordingly, increasing agglomeration manifests itself in a shift in the absorption maximum toward longer wavelengths, a decrease in absorption at maximum, and a broadening of the spectrum.

Appropriate resuspension experiments were carried out in which there are located, in a first tube, citrate-stabilized unmodified gold NP (1), in a second tube, AuNP that were modified with amino-C6-TTT-(SS)3 (abbreviated "(SS)3") using three coupled DTPA functions, and in a third tube, AuNP that were modified with 5' CCT CCT TTA CCG TGA TT-(SS)3, in each case after drying the (identically concentrated) solutions overnight in the vacuum centrifuge and subsequently 0.2% PEG-SH resuspended through simple agitation. Here, the observable intensity of the red coloring of the solution is directly proportional to the degree of resuspension.

Untreated citrate-stabilized AuNP are readily soluble when the salt content of the solution is low. However, with increasing salt concentration, also citrate-stabilized AuNP agglomerate. This can largely be avoided by modifying the AuNP with oligonucleotides, as depicted in FIG. 7:

FIG. 7 shows, in each case on the left, absorption spectra of various AuNP types in aqueous solution immediately after adding 6×PBS (reference signs 100, 102, 104) and the same solution after 120 min. (reference signs 110, 112, 114): top: citrate-stabilized unmodified AuNP; middle: amino-C6-TTT-(SS)3; bottom: AuNP that were modified with 5' CCT CCT TTA CCG TGA TT-(SS)3. In the right half of the image are shown, in each case, the differential spectra (reference signs 120, 122, 124). (PBS: phosphate buffered saline: 37 mM sodium chloride, 2.7 mM potassium chloride and 12 mM total phosphate (in the form of $HPO_4^{2-}$ and $H_2PO_4^-$); the pH level of the adjusted buffer solution is 7.4. The property as a buffer solution makes it possible to work at this constant pH value, and due to the different salts, the solution has the osmotic pressure in the human body—isotonic saline solution).

EXAMPLE 3: (MAXIMUM) COVERAGE DEPENDING ON THE ANCHOR FUNCTION/ACCESSIBILITY 1 ml citrate-stabilized AuNP (2.7 pmol) is realized with 5 nmol oligonucleotides (vide supra). The oligonucleotides have the different thiol anchor groups at the 3' end and fluorescein at the 5' end (abbreviations for thiol modifications of the oligonucleotides: "SH": simple thiol-modified oligonucleotides, HS—$(CH_2)_6$-oligo; "S": simple dithiol oligonucleotide R—S—S-oligo, here HO—$(CH_2)_6$—S—S—$(CH_2)_6$-oligo, "(SS)N, N=1 . . . 3": DTPA-modified oligonucleotides having a DTPA anchor, two or three directly covalently coupled DTPA functions).

The oligo sequence is always the same (5'-fluo-CCT CCT TTA CCG TGA TT-thiol), the oligos are used as a single strand (without complementary strand "GS", last row, reference sign 130 in FIG. 8), with short GS (5' TCA CCG TAA AGG, middle row, reference sign 132 in FIG. 8), hybridized or hybridized with completely complementary strand (5' CAA TCA CGG TAA AGG AGG; long GS, front row, reference sign 134 in FIG. 8). Following incubation of the AuNP with the respective oligos for 2 h, uncovered, free Au sites are "passivated" with PEG-SH (0.2%, 5 min) and the AuNP separated from the solution using centrifugation and resuspended in $H_2O$.

Thereafter, the concentrations of the particles are determined using UV-vis measurement (each approximately 0.2 pmol/ml) and 100 µl 0.1 M potassium cyanide solution are added to 300 µl of the particle suspension and incubated at room temperature for 1 h to dissolve the AuNP, similar to

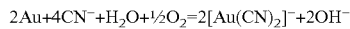

$$2Au+4CN^-+H_2O+\tfrac{1}{2}O_2=2[Au(CN)_2]^-+2OH^-$$

The red color of the gold NP disappears, the fluorophore-labeled oligonucleotides become available and their fluorescence is no longer quenched. The fluorescence-labeled oligonucleotide content is determined with the fluorometer. FIG. 8 shows the measurement results, the mutually correlated but non-standardized fluorescence intensity being shown along the y-axis.

EXAMPLE 4: TEMPERATURE STABILITY

FIG. 9 illustrates the temperature stability. Here, oligo-modified AuNP having a long (unlabeled) GS were used—as described for example 3—to determine the temperature stability of the different thiol anchor functions. The particles are heated up to the temperatures T indicated in FIG. 9, the temperature is maintained for 5 min. and the fluorescence of the solution is subsequently calculated, the (intrinsic) fluorescence of the solution at 20° C. being subtracted. The fluorescence increase obtained in this way, accumulated via the temperature increases, should therefore be generated exclusively by thermally removed 5' fluo-CCT CCT TTA CCG TGA TTG-thiol molecules in which the fluorescence of fluorescein is no longer quenched by the AuNP. The fluorescence depicted in FIG. 9 is, in addition, related to the particle concentration and the relative total coverage per particle and thus constitutes a mutually correlated but otherwise unstandardized thermal stability of the Au-thiol bonds.

As evident from FIG. 9, up to 40° C., all DTPA oligos (1-3 units, SS1, SS2, or SS3) are approximately identical and all more stable than the thiol oligos (SH and S—S). The relatively weak thermal stability of the simple DTPA anchor (SS)1 at temperatures of 60° C. and above seems unusual.

EXAMPLE 5: REACTIONS IN NON-AQUEOUS MEDIA

The (activation and) coupling of ligands cannot always be carried out in water/buffer, since nonpolar ligands are often insufficiently soluble in aqueous media, or some activation methods are not compatible with water.

Therefore, modified AuNP were manufactured for immunohistological dyes: Citrate-stabilized AuNP, $H_2N$-TTT-(SS)3-AuNP and $H_2N$-CCT CCT TTA CCG TGA TT-(SS)3-AuNP, each approximately 1.5 pmol in 1 mL are washed 2× with water (removing salts), and subsequently 4× with acetonitrile, and centrifuged. To the pellet are added 500 µl acetonitrile and 10 µl divinyl sulfone (DVS); under said conditions, the gold NP are not suspendable, they form a pellet or (in the case of citrate) a red layer on the wall of the Eppendorf tube.

The samples were then heated to 60° C. for 1 h (1,4 addition of a double bond of the DVS to OH (citrate) or $NH_2$). After cooling down to room temperature, they are washed 3× with acetonitrile, then taken up in water. It becomes clear that only the oligo-AuNP are suspendable, while the citrate-gold NP form a blue precipitate on the wall.

EXAMPLE 6

Further-functionalization of the DVS-activated gold NP in example 5: Addition of alkaline phosphatase/avidin conjugate to the activated double bond.

To each 500 µl 0.03 mg/ml DVS-activated or $H_2N$-CCT CCT TTA CCG TGA TT-(SS)3 AuNP in water are added 5 µl alkaline phosphatase/avidin conjugate (Sigma A7294) and incubated 24 h at RT. Thereafter, each is washed 4× with 500 µl water.

The coating of the oligo-modified AuNP with alkaline phosphatase/avidin can be determined by the attachment of biotin-4-fluorescein to said modified NP (assumptions: no fluorescence quenching, all 4 biotin binding sites of the avidin are accessible): A first tube contains alkaline-phosphatase-(AP)/avidin-conjugate-modified $H_2N$-TTT-(SS)3-AuNP: 3 AP/avidin per particle, a second tube, alkaline phosphatase-(AP)/avidin-conjugate-modified $H_2N$-CCT CCT TTA CCG TGA TT-(SS)3 AuNP: 15 AP/avidin per particle.

The activity of the AP is calculated via the addition of alkaline AP buffer and substrate (NBT, nitro blue tetrazolium chloride/BCIP, 5-Bromo-4-chloro-3-indolyl phosphate). 5 min. after the addition of NBT/BCIP, the color development in the first tube is more intense despite the higher number of AP/particles in the second tube.

To explain the activation with DVS: 1,4 addition; the activation of alcohols (ROH) is typically done non-aqueously at increased temperatures, the activation of amines (RNH$_2$) can be done aqueously or non-aqueously at RT.

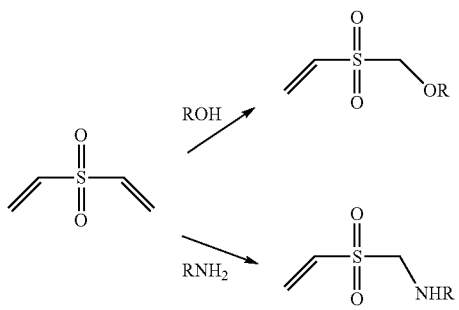

EXAMPLE 7: DETECTING MIRNA 146a IN MACROPHAGES WITH A STANDARDIZED AUNP BUILDING BLOCK

Macrophages that were stimulated to express miRNA 146a were incubated with 15 nm gold NP. The gold NP were functionalized as follows:

5'ACT GAA TTC CAT GGG TT-Cy3 CCT CCT TTA CCG TGA TTG (SS)3-Au-NP AC TCT TGA CTT AAG GTA CCC AA G GGA GGA AAT GGC ACT AAC

These can easily be obtained by means of the readily water-soluble AuNP building blocks CCT CCT TTA CCG TGA TTG (SS)3-AuNP (manufactured similarly to example 1) through sequential or simultaneous incubation with the splint (3'AC TCT TGA CTT AAG GTA CCC AAG GGA GGA AAT GGC ACT AAC) and target (5' ACT GAA TTC CAT GGG TT-Cy3) sequences. The target sequence ACT GAA TTC CAT GGG TT-Cy3 is complementary to the sought-after miRNA 146a of the macrophages and is displaced from the adduct if miRNA 146a is present in the adduct. In this case, the Cy3 fluorescence that is otherwise quenched by the AuNP becomes visible.

FIG. 10 shows, in a), a transmitted-light image, and in b), a fluorescence microscopy image of a macrophage, it being clearly evident from the fluorescence 140 visible in FIG. 10 b) that the chosen approach using the AuNP building block works.

Further embodiments of the present invention:

EMBODIMENT 1

A prefunctionalized metallic nanoparticle as a standardized basic building block of biofunctionalized nanoparticles, having a thiol-reactive metallic nanoparticle that is prefunctionalized by a bifunctional molecule that consists of an anchor component and a short further-functionalization stub,
  the anchor component comprising one or more dithiophosphate groups, and
  the short further-functionalization stub being adapted for the attachment of a desired biofunctionalization and being selected from the group consisting of i) a standardized oligonucleotide strand having 2 to 18 bases for further-functionalization with biomolecules having a terminal complementary strand of the standardized oligonucleotide strand,
ii) a 1- to 4-base-long oligonucleotide having an alkyne terminus for further-functionalization with azide-terminated biomolecules, and
iii) a 1- to 4-base-long oligonucleotide having terminal Ni-nitrilo acetic acid for further-functionalization with His-tag-terminated biomolecules.

EMBODIMENT 2

The prefunctionalized metallic nanoparticle according to embodiment 1, characterized in that, in case i), the oligonucleotide strand has a melting temperature above 40° C., preferably between 40° C. and 70° C.

EMBODIMENT 3

The prefunctionalized metallic nanoparticle according to embodiment 1 or 2, characterized in that, in case i), the oligonucleotide strand is non-coding, especially non-human-genome-coding.

EMBODIMENT 4

The prefunctionalized metallic nanoparticle according to at least one of embodiments 1 to 3, characterized in that, in case i), more than 60%, preferably more than 65%, particularly preferably more than 70% of the bases of the oligonucleotide strand are guanine and/or cytosine.

EMBODIMENT 5

A prefunctionalized metallic nanoparticle according to at least one of embodiments 1 to 4, characterized in that the nanoparticle is provided with multiple bifunctional molecules having the same further-functionalization stub.

EMBODIMENT 6

The prefunctionalized metallic nanoparticle according to at least one of embodiments 1 to 4, characterized in that the nanoparticle comprises two, three or four different bifunctional molecules, each having a different standardized further-functionalization stub.

EMBODIMENT 7

The prefunctionalized metallic nanoparticle according to at least one of embodiments 1 to 6, characterized in that, aside from the bifunctional molecules, the metallic surface of the nanoparticle is provided with a passivation, especially using alkane thiols or polyethylene glycols.

EMBODIMENT 8

A biofunctionalized metallic nanoparticle in which a biomolecule is attached to the further-functionalization stub of a prefunctionalized metallic nanoparticle according to one of embodiments 1 to 7.

EMBODIMENT 9

A method for manufacturing a biofunctionalized metallic nanoparticle in which a biomolecule is attached to the further-functionalization stub of a prefunctionalized metallic nanoparticle according to one of embodiments 1 to 7.

EMBODIMENT 10

A use of prefunctionalized metallic nanoparticles according to one of embodiments 1 to 7 for attaching biomolecules.

EMBODIMENT 11

The nanoparticle, method or use according to embodiment 8, 9 or 10, characterized in that the biomolecule is formed by a nucleic acid oligomer, especially a single- or partially double-stranded nucleic acid oligomer or a protein.

EMBODIMENT 12

A nanoparticle kit for manufacturing biofunctionalized nanoparticles that includes prefunctionalized metallic nanoparticles as standardized basic building blocks, and in which each basic building block is formed by a thiol-reactive metallic nanoparticle that is prefunctionalized by one or more bifunctional molecules, each of which consists of an anchor component and a short further-functionalization stub,
  the anchor component for each bifunctional molecule of a basic building block comprising one or more dithiophosphate groups,
  the short further-functionalization stub for each bifunctional molecule of a basic building block being adapted for the attachment of a desired biofunctionalization and consisting of an oligonucleotide strand having 2 to 18 bases for further-functionalization with biomolecules having a terminal complementary strand of the oligonucleotide strand, and
  the oligonucleotide strand of each of the bifunctional molecules of a basic building block being selected from a basic set of predetermined oligonucleotide strands that includes four or fewer oligonucleotide strands.

EMBODIMENT 13

The nanoparticle kit according to embodiment 12, characterized in that the nanoparticle kit
  includes first standardized basic building blocks whose bifunctional molecules include only one different further-functionalization stub, which is formed by a first oligonucleotide strand from the mentioned basic set, and
  includes second standardized basic building blocks whose bifunctional molecules include exactly two different further-functionalization stubs, which are formed by the mentioned first oligonucleotide strand and a second oligonucleotide strand from the mentioned basic set.

EMBODIMENT 14

The nanoparticle kit according to embodiment 13, characterized in that the nanoparticle kit further
  includes third standardized basic building blocks whose bifunctional molecules include exactly three different further-functionalization stubs, which are formed by the mentioned first and second oligonucleotide strand and a third oligonucleotide strand from the mentioned basic set.

EMBODIMENT 15

The nanoparticle kit according to embodiment 14, characterized in that nanoparticle kit further
  includes fourth standardized basic building blocks whose bifunctional molecules include exactly four different further-functionalization stubs, which are formed by the mentioned first, second and third oligonucleotide strand and a fourth oligonucleotide strand from the mentioned basic set.

EMBODIMENT 16

The nanoparticle kit according to at least one of embodiments 12 to 15, characterized in that the nanoparticle kit includes basic building blocks having a different particle size and/or a different thermal and/or chemical stability of the anchored further-functionalization stubs and/or a different coverage density with the bifunctional molecules and/or a different coadsorbate for passivation.

---

The invention claimed is:

1. A prefunctionalized metallic nanoparticle adapted as a standardized basic element of biofunctionalized nanoparticles, having a thiol-reactive metallic nanoparticle that is prefunctionalized by a bifunctional molecule that consists of an anchor component and a short further-functionalization stub,
   the anchor component comprising one or more dithiophosphate groups, and
   the short further-functionalization stub being adapted for the attachment of a desired biofunctionalization and being
   a 2- to 18-base-long oligonucleotide strand that is modified with a terminal reactive group for biomolecules.

2. The prefunctionalized metallic nanoparticle according to claim 1, wherein the terminal reactive group is an alkyne terminus for further-functionalization with azide-terminated biomolecules, Ni-nitrilo acetic acid for further-functionalization with His-tag-terminated biomolecules, or a biotin terminus for further-functionalization with avidin-terminated biomolecules.

3. The prefunctionalized metallic nanoparticle according to claim 1, further wherein the unmodified standardized oligonucleotide strand is selected in such a way that the prefunctionalized metallic nanoparticle is storage stable.

4. The prefunctionalized metallic nanoparticle according to claim 1, wherein the terminal reactive group is a biotin terminus for further-functionalization with avidin-terminated biomolecules.

5. The prefunctionalized metallic nanoparticle according to claim 1, wherein the terminal reactive group is an Ni-nitrilo acetic acid for further-functionalization with His-tag-terminated biomolecules.

6. The prefunctionalized metallic nanoparticle according to claim 1, wherein more than 60% of the bases of the oligonucleotide strand are guanine and/or cytosine.

7. The prefunctionalized metallic nanoparticle according to claim 1, wherein the nanoparticle comprises multiple bifunctional molecules having the same further-functionalization stub, or wherein the nanoparticle comprises two, three or four different bifunctional molecules, each having a different standardized further-functionalization stub.

8. The prefunctionalized metallic nanoparticle according to claim 1, wherein aside from the bifunctional molecules, the metallic surface of the nanoparticle is provided with a passivation, by reaction with alkane thiols or polyethylene glycols.

9. The prefunctionalized metallic nanoparticle according to claim 1, wherein the prefunctionalized metallic nanoparticle is further-functionalizable through simple incubation with anchor-modified oligonucleotides in aqueous or non-aqueous medium.

10. A biofunctionalized metallic nanoparticle in which a biomolecule is attached to the further-functionalization stub of a prefunctionalized metallic nanoparticle according to claim 1.

11. The prefunctionalized metallic nanoparticle according to claim 10 wherein the biomolecule is formed by reacting the biofunctionalized metallic nanoparticle with a single- or partially double-stranded nucleic acid oligomer.

12. A method for manufacturing a biofunctionalized metallic nanoparticle comprising attaching a biomolecule to the further-functionalization stub of a prefunctionalized metallic nanoparticle according to claim 1 to form the biofunctionalized metallic nanoparticle.

13. The method of claim 12 wherein the biomolecule has been prepared with a terminal complimentary strand.

14. The prefunctionalized metallic nanoparticle according to claim 1, wherein the nanoparticle comprises two, three or four different bifunctional molecules, each having a standardized further-functionalization stub that is different than the short further-functionalization stub.

15. A nanoparticle kit for manufacturing biofunctionalized nanoparticles comprising prefunctionalized metallic nanoparticles as standardized basic elements, and in which each basic element is formed by a thiol-reactive metallic nanoparticle that is prefunctionalized by one or more bifunctional molecules, each of which consists of an anchor component and a short further-functionalization stub,
  the anchor component for each bifunctional molecule of a basic building block comprising one or more dithiophosphate groups,
  the short further-functionalization stub for each bifunctional molecule of a basic building block being adapted for the attachment of a desired biofunctionalization and consisting of an oligonucleotide strand having 2 to 18 bases for further-functionalization with biomolecules having a terminal complementary strand of the oligonucleotide strand, and
  the oligonucleotide strand of each of the bifunctional molecules of a basic building block being selected from a basic set of predetermined oligonucleotide strands that includes four or fewer oligonucleotide strands.

16. The nanoparticle kit according to claim 15,
  comprising first standardized basic elements whose bifunctional molecules include only one different further-functionalization stub, which is formed by a first oligonucleotide strand from the mentioned basic set, and
  comprising second standardized basic building blocks whose bifunctional molecules include exactly two different further-functionalization stubs, which are formed by the mentioned first oligonucleotide strand and a second oligonucleotide strand from the mentioned basic set.

17. The nanoparticle kit according to claim 16, characterized in that the nanoparticle kit further
  includes third standardized basic building blocks whose bifunctional molecules include exactly three different further-functionalization stubs, which are formed by the mentioned first and second oligonucleotide strand and a third oligonucleotide strand from the mentioned basic set.

18. The nanoparticle kit according to claim 17, characterized in that the nanoparticle kit further includes fourth standardized basic building blocks whose bifunctional molecules include exactly four different further-functionalization stubs, which are formed by the mentioned first, second and third oligonucleotide strand and a fourth oligonucleotide strand from the mentioned basic set.

19. The nanoparticle kit according to claim 15, characterized in that the nanoparticle kit includes basic building blocks having different particle sizes and/or a different thermal and/or chemical stability of the anchored further-functionalization stubs and/or a different coverage density with the bifunctional molecules and/or a different coadsorbate for passivation.

20. A kit comprising a prefunctionalized metallic nanoparticle and at least one biomolecule adapted to be attached to the nanoparticle, wherein
  the prefunctionalized metallic nanoparticle comprises a thiol-reactive metallic nanoparticle and a bifunctional molecule consisting of an anchor component and a short further-functionalization stub, the thiol-reactive metallic nanoparticle being prefunctionalized by the bifunctional molecule, wherein
  the anchor component comprises one or more dithiophosphate groups, and
  the short further-functionalization stub is an unmodified standardized oligonucleotide having
  a useful region with a desired biofunctionalization and
  a terminal strand attached to the useful region, which is complementary to the short further-functionalization stub of the prefunctionalized metallic nanoparticle.

21. The kit of claim 20 comprising a plurality of prefunctionalized metallic nanoparticles each having the same short further-functionalization stub, and a plurality of biomolecules adapted to be attached to the nanoparticles, wherein the biomolecules all have the same terminal strand complementary to the short further-functionalization stub of the prefunctionalized metallic nanoparticles, but have different useful regions.

* * * * *